(12) United States Patent
Amanatullah

(10) Patent No.: US 10,758,395 B2
(45) Date of Patent: *Sep. 1, 2020

(54) DYNAMIC HALLUX TENSION DEVICE FOR TREATMENT OF PLANTAR FASCIITIS

(71) Applicant: Arthrology Designs, LLC, Palo Alto, CA (US)

(72) Inventor: Derek Amanatullah, Palo Alto, CA (US)

(73) Assignee: Arthrology Designs, LLC, Palo Alto, CA (US)

(*) Notice: Subject to any disclaimer, the term of this patent is extended or adjusted under 35 U.S.C. 154(b) by 531 days.

This patent is subject to a terminal disclaimer.

(21) Appl. No.: 15/686,515

(22) Filed: Aug. 25, 2017

(65) Prior Publication Data

US 2018/0028342 A1    Feb. 1, 2018

Related U.S. Application Data

(63) Continuation of application No. 15/098,696, filed on Apr. 14, 2016, now Pat. No. 9,750,631, which is a
(Continued)

(51) Int. Cl.
*A61F 5/00* (2006.01)
*A61F 13/00* (2006.01)
(Continued)

(52) U.S. Cl.
CPC ............ *A61F 5/019* (2013.01); *A61F 5/0111* (2013.01); *A61F 5/042* (2013.01); *A61F 5/0585* (2013.01)

(58) Field of Classification Search
CPC ...... A61F 13/064; A61F 13/08; A61F 13/066; A61F 13/069; A61F 5/0111; A61F 13/06; A61F 13/067; A61F 13/10; A61F 13/00063; A61F 2013/0028; A61F 13/00021; A61F 13/068; A61F 13/104; A61F 2013/00404; A61F 13/00017; A61F 13/00038; A61F 13/00068; A61F 2013/00093; A61F 2013/00119; A61F 5/0127; A61F 13/0216; A61F 13/061; A61F 13/065; A61F 13/12; A61F 15/004; A61F 2013/0091;
(Continued)

(56) References Cited

U.S. PATENT DOCUMENTS 643,068 A * 2/1900 Pond ........................ A61F 5/019
602/30
2,523,606 A    9/1950 Young
(Continued)

FOREIGN PATENT DOCUMENTS

GB    344590 A    3/1931
GB   2281023 A    2/1995

*Primary Examiner* — Kim M Lewis
(74) *Attorney, Agent, or Firm* — Knobbe, Martens, Olson & Bear, LLP

(57) ABSTRACT

A physical rehabilitation device for the treatment of a medical condition of the foot known as plantar fasciitis includes a splint which is connected to the toe and ankle of a patient. The splint can be used in a method for treating plantar fasciitis known as "dynamic splinting". This device allows the patient to bend the ankle and thus dynamically change the flexion in the foot of the patient. The device itself is unique, but the method of treatment made possible by this device is also unique.

17 Claims, 4 Drawing Sheets

Related U.S. Application Data continuation of application No. 13/745,768, filed on Jan. 19, 2013, now Pat. No. 9,320,637.

(51) Int. Cl.
*A61F 5/01* (2006.01)
*A61F 5/058* (2006.01)
*A61F 5/042* (2006.01)

(58) Field of Classification Search
CPC .. A61F 5/30; A61F 13/00029; A61F 13/0259; A61F 13/085; A61F 2013/00272; A61F 2013/00578; A61F 5/01; A61F 13/00051; A61F 13/00085; A61F 13/0206; A61F 13/0253; A61F 13/101; A61F 13/51456; A61F 17/00; A61F 2013/00157; A61F 2013/00748; A61F 5/019; A61F 7/02; A61F 13/00012; A61F 13/00042; A61F 13/00046; A61F 13/023; A61F 13/041; A61F 13/107; A61F 13/108; A61F 2013/00246; A61F 2013/00285; A61F 2013/00387; A61F 2013/00604; A61F 5/00; A61F 5/37; A61F 7/00; A61F 13/0213; A61F 13/062; A61F 13/105; A61F 13/5323; A61F 15/006; A61F 2013/00097; A61F 2013/00102; A61F 2013/00127; A61F 2013/00144; A61F 2013/00148; A61F 2013/00182; A61F 2013/00374; A61F 2013/00382; A61F 2013/0048; A61F 2013/00519; A61F 2013/00523; A61F 2013/0054; A61F 2013/00548; A61F 2013/00557; A61F 2013/0057; A61F 2013/00846; A61F 2013/00855; A61F 5/0106; A61F 5/0585; A61F 13/00; A61F 13/0209; A61F 13/022; A61F 13/0269; A61F 13/0283; A61F 13/122; A61F 13/14; A61F 13/143; A61F 13/148; A61F 13/2002; A61F 13/581; A61F 2002/7818; A61F 2002/785; A61F 2002/7881; A61F 2007/0045; A61F 2013/00123; A61F 2013/00174; A61F 2013/00187; A61F 2013/00238; A61F 2013/00476; A61F 2013/00489; A61F 2013/00497; A61F 2013/00502; A61F 2013/00574; A61F 2013/00697; A61F 2013/00817; A61F 2013/00906; A61F 2013/8497; A61F 2/78; A61F 2/7812; A61F 13/0203; A61F 13/0236; A61F 13/024; A61F 13/0243; A61F 13/0246; A61F 13/025; A61F 13/0266; A61F 13/0289; A61F 13/04; A61F 13/063; A61F 13/102; A61F 13/15; A61F 15/008; A61F 2005/0172; A61F 2005/0174; A61F 2007/0043; A61F 2007/0044; A61F 2007/0046; A61F 2007/0228; A61F 2007/0238; A61F 2007/0242; A61F 2007/108; A61F 2013/0011; A61F 2013/00153; A61F 2013/00217; A61F 2013/00289; A61F 2013/00395; A61F 2013/00468; A61F 2013/00536; A61F 2013/00561; A61F 2013/00565; A61F 2013/00608; A61F 2013/00663; A61F 2013/0071; A61F 2013/00723; A61F 2013/00727; A61F 2013/00744; A61F 2013/00761; A61F 2013/00834; A61F 2013/00868; A61F 2013/00936; A61F 2013/15024; A61F 5/14; A61F 5/32; A61F 5/34; A61F 5/40; A61F 7/10

See application file for complete search history.

(56) References Cited

U.S. PATENT DOCUMENTS

| | | | | |
|---|---|---|---|---|
| 2,596,038 | A * | 5/1952 | Mayer | A61F 5/019 602/30 |
| 3,049,120 | A * | 8/1962 | Edith Marcus | A61F 5/019 602/30 |
| 3,063,446 | A * | 11/1962 | Levitt | A61F 5/019 602/30 |
| 3,219,032 | A * | 11/1965 | Levitt | A61F 5/019 602/30 |
| 4,329,982 | A | 5/1982 | Heaney | |
| 4,566,447 | A | 1/1986 | Deis | |
| 4,644,940 | A | 2/1987 | Nakamura | |
| 4,869,499 | A | 9/1989 | Schiraldo | |
| 5,257,969 | A | 11/1993 | Mance | |
| 5,772,621 | A | 6/1998 | Unruh | |
| 6,908,445 | B2 | 6/2005 | Watts | |
| 7,396,338 | B2 * | 7/2008 | Huber | A61F 5/0102 128/893 |
| 7,996,924 | B2 | 8/2011 | Wright | |
| 8,663,178 | B2 * | 3/2014 | De Luca | A61F 5/019 604/293 |
| 9,320,637 | B2 * | 4/2016 | Amanatullah | A61F 5/0111 |
| 9,750,631 | B2 * | 9/2017 | Amanatullah | A61F 5/0111 |
| 2005/0186387 | A1 | 8/2005 | Gallant | |
| 2009/0062714 | A1 | 3/2009 | Trujillo | |
| 2009/0264803 | A1 * | 10/2009 | Darby, II | A61F 5/019 602/27 |
| 2010/0262057 | A1 | 10/2010 | Chandrasekar | |
| 2013/0060181 | A1 * | 3/2013 | Fontaine | A61F 13/064 602/30 |
| 2013/0276331 | A1 | 10/2013 | Steel | |

\* cited by examiner

DYNAMIC HALLUX TENSION DEVICE FOR TREATMENT OF PLANTAR FASCIITIS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57 and should be considered a part of this specification.

BACKGROUND

Field

The present invention pertains to medical devices for the treatment of orthopedic injuries, and more particularly relates to a physical rehabilitation device for the treatment of a medical condition of the foot known as plantar faciitis.

Description of the Related Art

The plantar fascia (plantar aponeurosis) is a bowstring that connects the metatarsal heads and the medial border of the calcaneus 9 (see FIG. 2). When taut, this bowstring supports the longitudinal arch of the foot. Because of the insertion of the plantar fascia into the metatarsal heads, when the toes are dorsiflexed the plantar fascia tightens. This phenomenon is known as the Windlass effect. The Windlass effect is utilized during normal ambulation (i.e., gait). During the toe-off phase of gait the hallux (great or first toe) is extended to lock the longitudinal arch of the foot and provide a solid foundation for propulsion of the leg through the swing phase of gait. Hence, any extension of the hallux tenses the plantar fascia and locks the longitudinal arch.

The disease this device supports is described as follows. Plantar fasciitis and heel spurs are related and common ailments that involve inflammation and damage to the plantar fascia. This usually occurs as a result of repetitive trauma and cumulative micro-damage resulting in degeneration of the plantar fascia during stress of the longitudinal arch of the foot (i.e., running, dancing, ballet, martial arts, etc.). The degeneration of the plantar fascia results in heel and/or metatarsal pain during weight bearing activities.

Since the resting tone of foot flexors (i.e., plantar flexors) exceeds that of the foot extensors (i.e., dorsiflexors), the foot assumes a plantar position while at rest. This plantar positioning of the foot at night results in relaxation of the plantar fascia. Micro-damage within the plantar fascia begins to heal in a relaxed position. Since healing cannot be completed as re-tearing occurs when the plantar fascia is tensed with the first step of the day (i.e., during toe-off during the gait cycle) creating the hallmark sign of plantar fasciitis—metatarsal or heel pain with the first step in the morning. The resulting cycle of partial healing and repetitive trauma exacerbates the pain and inflammation of plantar fasciitis. Hence, allowing the plantar fascia to heal in a tensed position will result in pain relief, decreased inflammation, and repair of the micro-damage resulting from repetitive foot trauma.

Existing devices for treatment of plantar fasciitis include therapy, massage, ice, and anti-inflammatory medications. Existing splints for the treatment of plantar fasciitis secure the great toe in one place and fix the ankle at a 90 degree angle. Traditionally, plantar fasciitis has been treated with static tibiotalar dorsiflexion or static hallux dorsiflexion at night. Both of these modes of treatment tense the plantar fascia, but neither allows for increasing dynamic tension to be applied to the plantar fascia with increased ankle plantar flexion, full and complete range of motion of the second through fifth metatarsophalangeal, tibiotalar, or subtalar joints, and minimal coverage of the foot allowing for normal heat and moisture exchange. Note that current static hallux dorsiflexion splints do not allow free second through fifth metatarsophalangeal or subtalar joint motion. All of these issues become critical, because while either form of static splinting is effective, it is normally not a practical solution to plantar fasciitis.

Few patients are compliant with static night splinting rendering these treatments practically ineffective. Static splinting interferes with the ability to ambulate normally because of static restrictions placed on the mobility of the metatarsophalangeal, tibiotalar, or subtalar joints. In addition, these splints are too bulky and interfere with normal temperature or moisture exchange at the level of the foot making sleep in these splints very uncomfortable. Lastly, static splinting results in an uncomfortable burning sensation on the plantar surface of the foot as a result of a static continuous stretch placed on an already inflamed plantar fascia. Hence, the development of a low profile dynamic tension plantar fascia splint or sock is required to increase patient compliance and treat plantar fasciitis. This medical device allows for this alternative form of treatment of dynamic splinting and thus results in improved night treatment of plantar fasciitis.

SUMMARY

The medical device disclosed herein is a significant improvement over previous splints for treatment of plantar fasciitis. The splint allows for dynamic tension treatment of plantar fasciitis, and does not secure the great toe in a fixed position or the ankle at a 90 degree angle, thus allowing for dynamic splinting of the great toe. This medical device allows for this alternative form of treatment of dynamic splinting and thus results in improved night treatment of plantar fasciitis.

The mechanical device disclosed herein is a significant improvement over previous devices because it allows for "dynamic splinting." Dynamic splinting allows a patient to control the amount of tension on the great toe because the splint does not fix the ankle in place and instead allows the ankle to dorsiflex and plantarflex as desired by the patient. More specifically, if the dynamic tension splint is applied and the patient dorsiflexes the ankle, tension on the great toe will be relieved and the plantar fascia will be under less tension. Alternatively, if the dynamic tension splint is applied and the patient plantarflexes the ankle, tension on the great toe will be increased and the plantar fascia will be under more tension. Additionally, dynamic splinting allows active plantar flexion of the great toe and ankle via flexor hallucis longus or the gastrocnemius-soleus complex to overcome the elastic tension on the great toe, permitting unencumbered normal ambulation with the dynamic splint in place. The device consists of a sling made of elastic or other comparable material which pulls back the great toe of the foot by connecting the great toe of the foot to the ankle of the same foot via a helix. The device is secured around the ankle by a VELCRO® hoop and loop fastener or other fastening device. In addition to these two mechanical benefits, dynamic splinting makes daily use of a splint possible for the first time. The minimal profile of this splint also addresses the current issues with splint bulk and temperature or moisture variations on the foot. This minimal profile thus allows the splint to address the pain and disability of plantar fasciitis as well as the patient compliance issues that plague the current static treatments for plantar fasciitis. The present invention is a device that can be worn daily within traditional shoe wear for the relief of the pain and disability associated with plantar fasciitis.

A first embodiment of the invention includes a cloth and elastic strap that fits over the great toe of a patient's foot and is secured around the ankle. A second embodiment includes the first embodiment with a cloth or elastic sock either fit under the device or incorporated into the device. The device works by pulling the great toe toward the shin of the patient. The method of using these two embodiments of the medical device enables treatment known as dynamic tension treatment. This device, in contrast to previous devices, allows the patient freedom of movement in the great toe and ankle. The device does not secure the great toe in a fixed position or the ankle at a 90 degree angle. Instead, the patient is allowed range of motion and is thus able to walk and vary the extension applied to the great toe.

BRIEF DESCRIPTION OF THE DRAWINGS

Further features, properties and advantages of the present invention will become clear from the following description of embodiments in conjunction with the accompanying drawings. The described features are advantages alone and in combination with each other.

DETAILED DESCRIPTION

Figure 1:
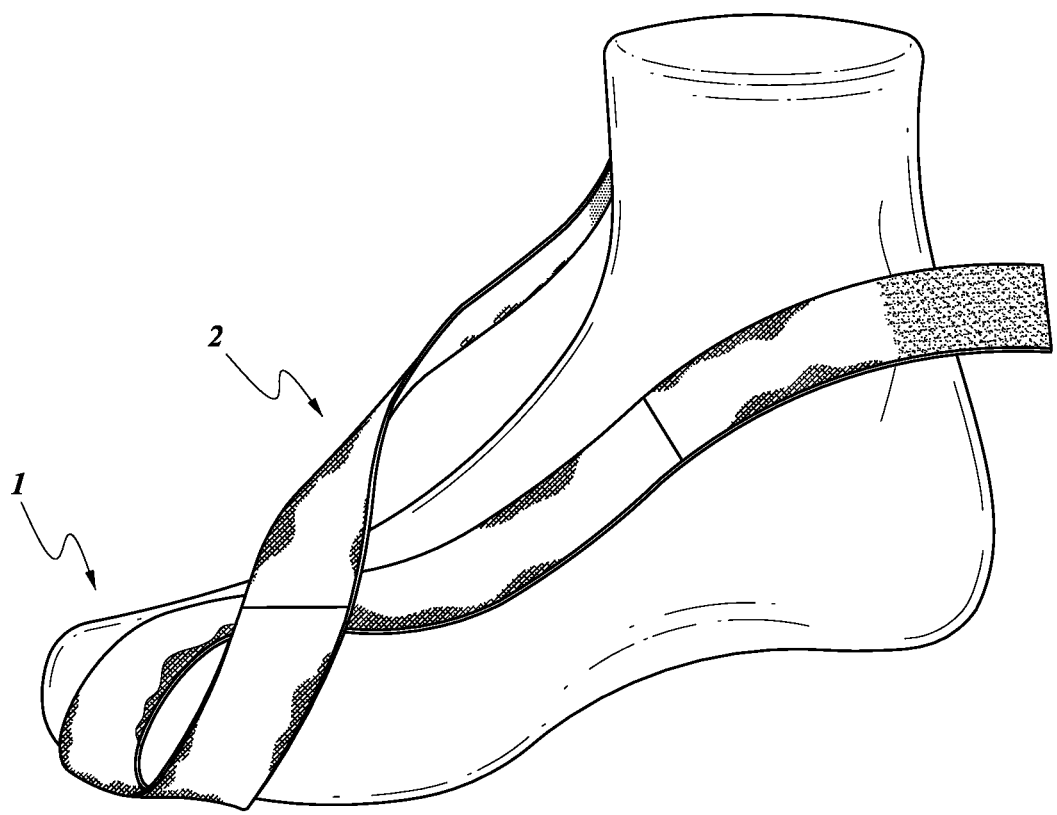
FIG. 1 shows an isometric view of the main components of the first embodiment of the device over a foot.
Figure 2:
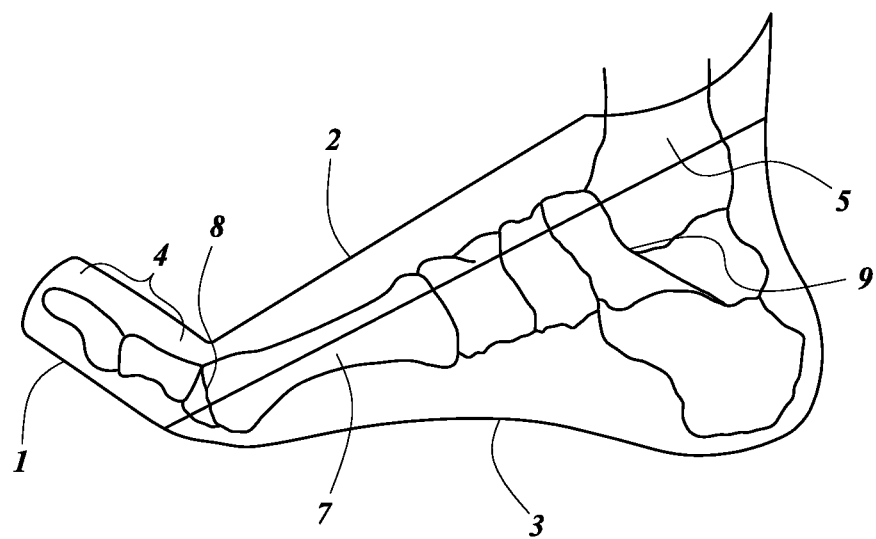
FIG. 2 shows a medial view of an assembled device over the bones of the foot.
Figure 3:
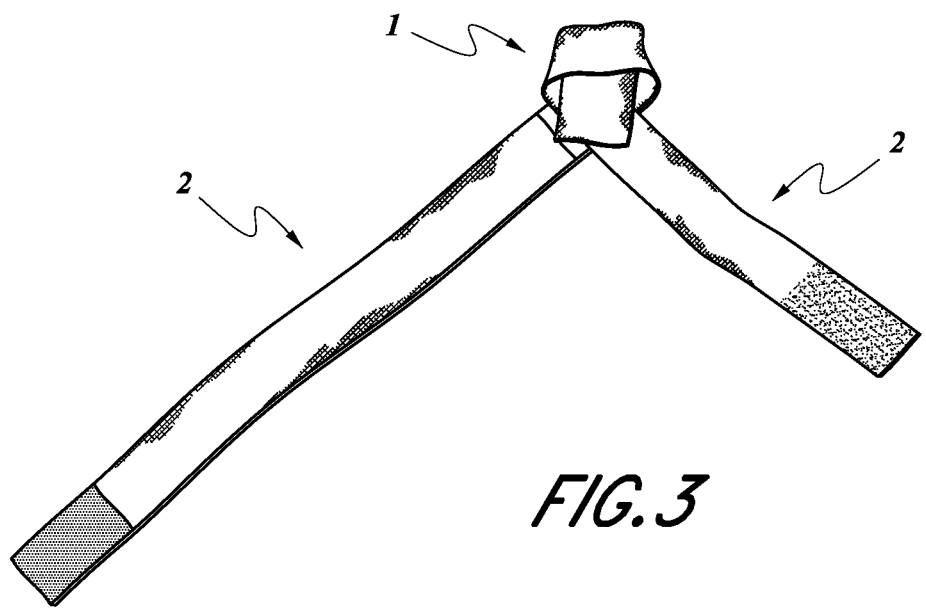
FIG. 3 shows the medical device without a sock not attached to a patient and laid out in a resting position.
Figure 4:
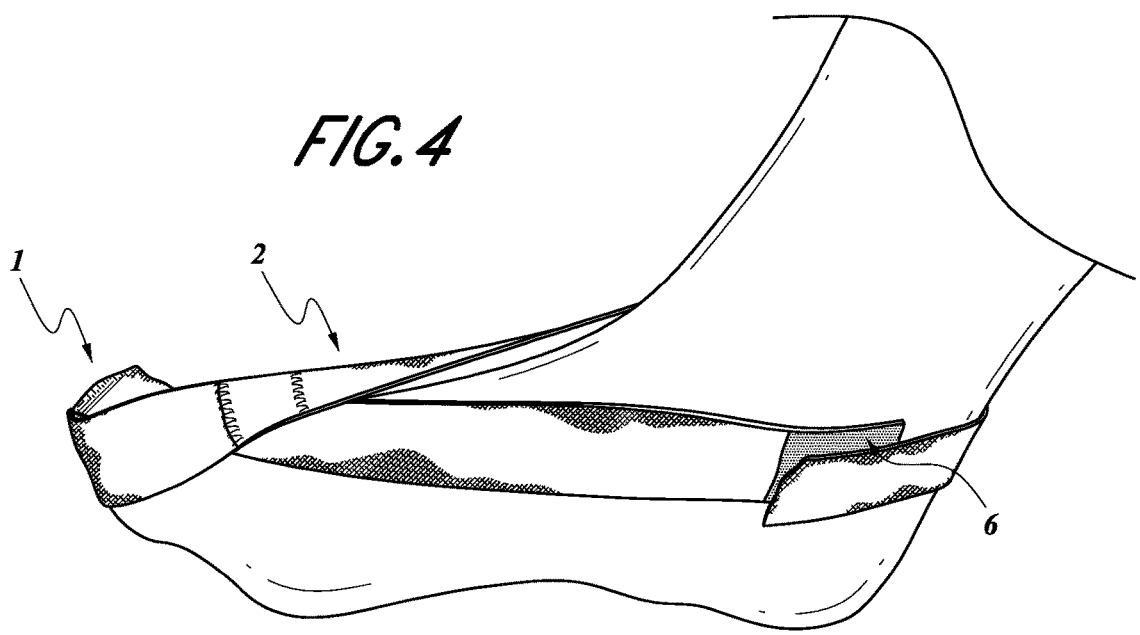
FIG. 4 shows an Isometric view of the actual mechanical device without sock.
Figure 5:
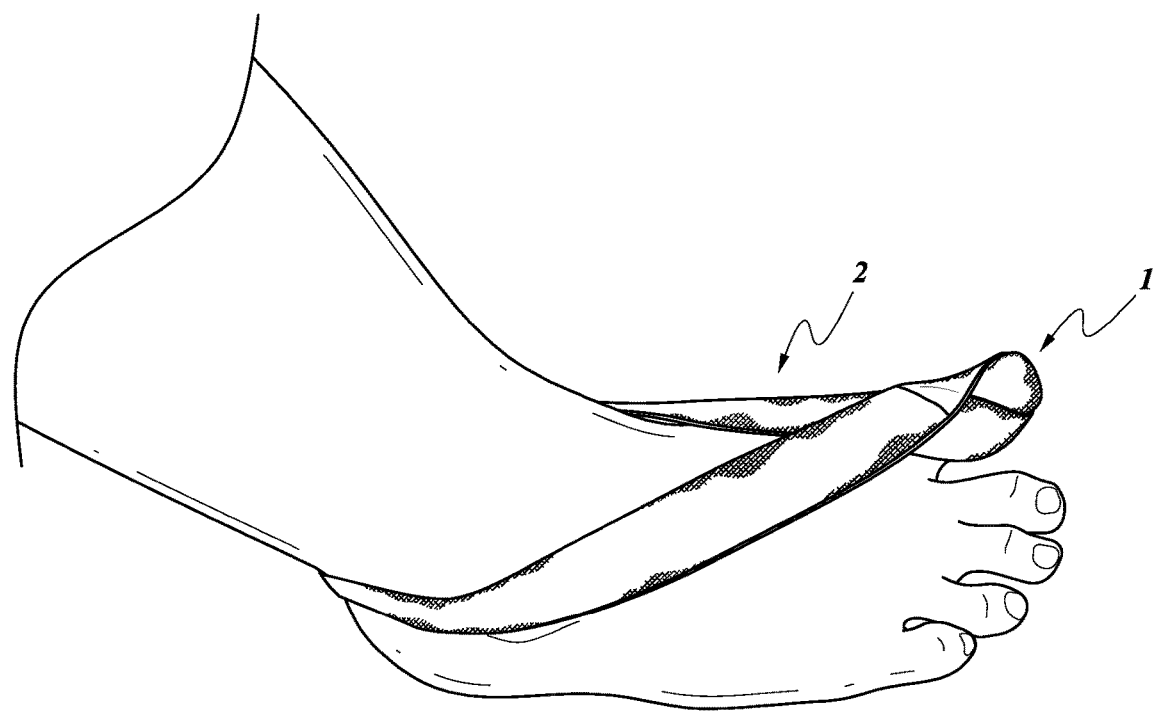
FIG. 5 shows a top view of actual mechanical device without sock.

A first embodiment of a dynamic tension device is illustrated in FIGS. 1-5 and 7 (medial view of device over the bones of the foot). The device utilizes a hallux sling 1 (FIG. 2), which is a stiff elastic band consisting of a nylon blend, although it is not limited to this material, wrapped around the plantar surface of the hallux 4 (FIG. 2). The second toe may also be included in the hallux sling 1 (FIG. 2).

The hallux sling 1 (FIG. 2) is secured to the ankle 5 (FIG. 2) via the ankle sling 2 (FIG. 2). The ankle sling 2 (FIG. 2) is another stiff elastic band, which is composed of the same material as the hallux sling 1 (FIG. 2), although it may be composed of a different material. The ankle sling 2 (FIG. 2) is less stiff than the hallux sling 1 (FIG. 2) and is wrapped around the ankle 5 (FIG. 2).

Figure 6:
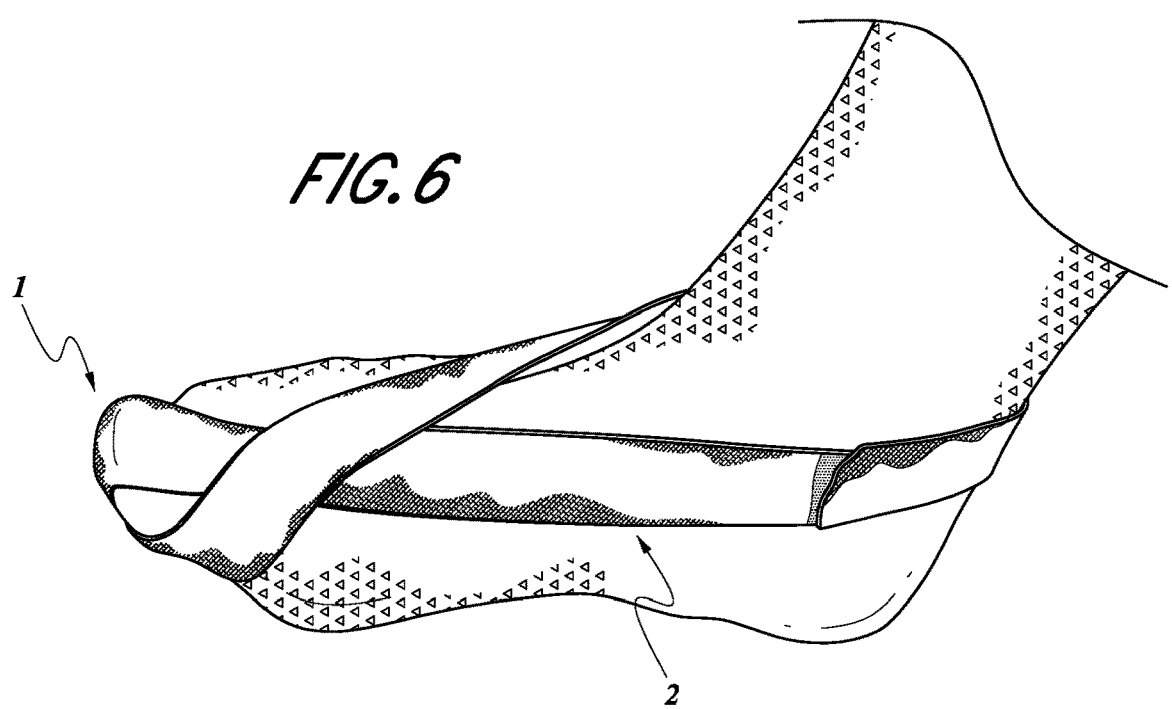
FIG. 6 shows Isometric view of mechanical device with sock.

A second embodiment of the invention includes the first embodiment of the invention, in addition to a sock as shown in FIG. 6. Alternatively, the remainder of the dynamic tension device is filled in with a flexible material 3 (see e.g., FIG. 2), such as a cotton-blend, to mimic a sock, although it may be composed of another flexible material, or the remainder can be left empty based on the desired design and function.

The operation of the device is illustrated in the following FIGS. 1,3,4,5,6 and 7.

The device is simple in design. It is composed of a hallux (big toe) sling 1 made of an elastic band and cotton or other similar materials which is secured to itself by a VELCRO® hoop and loop fastener—or other similar material. The hallux sling 1 is in the form of a helix. A hallux sling 1 of the first embodiment of the invention, without a sock, is shown over a foot in FIG. 1.

Figure 7:
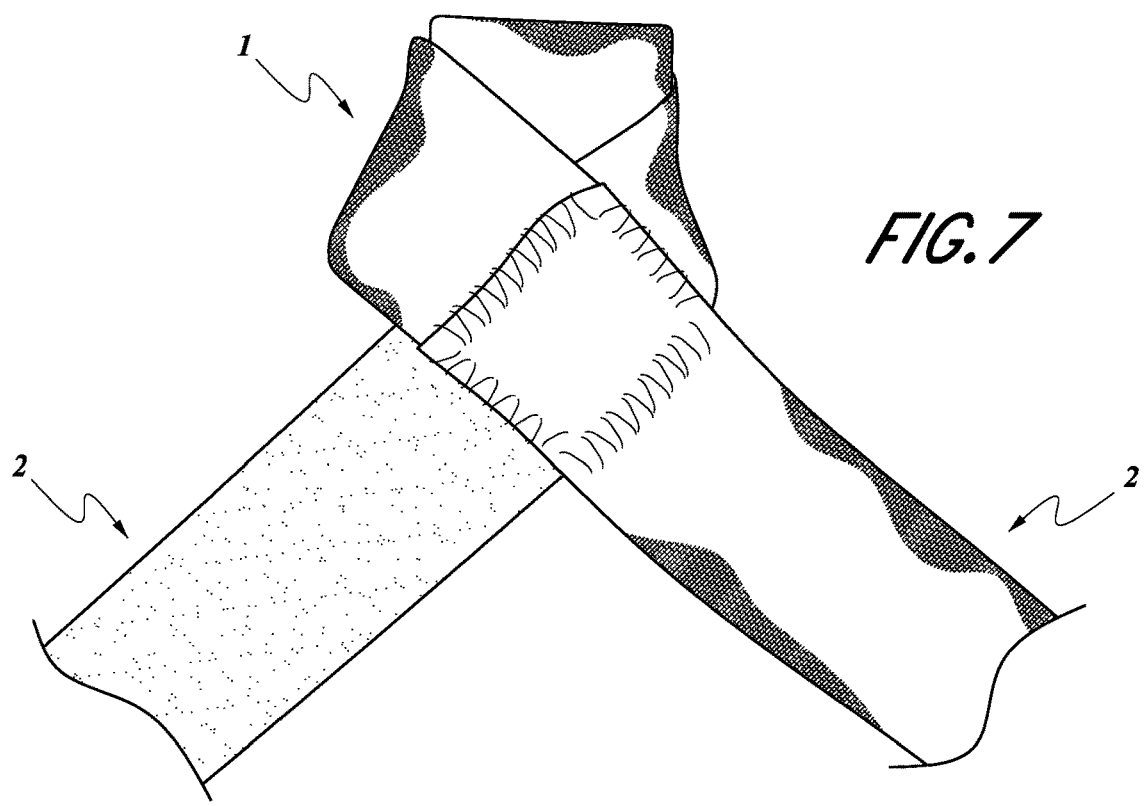
FIG. 7 shows a close-up view of the helix which fits over the large toe (hallux) of the patient.

A close view of the hallux loop (helix) of the device is shown in FIG. 7. As shown the helix can include a second piece of elastic or other comparable material to increase comfort for the patient. The loop is composed of an elastic band sewn to a cloth band. These combined bands form a loop or "helix" and turn back in to be secured by a VELCRO® hoop and loop fastening device.

This device utilizes a hallux sling 1 (FIG. 2), composed of an elastic band, wrapped around the plantar surface of the hallux 4 (FIG. 2) but not including the metatarsophalangeal joint 8 (FIG. 2) between the first metatarsal 7 and the hallux 4 to provide the force of dorsiflexion required to overcome the resting strength of the flexor hallicus longus and result in passive hallux dorsiflexion. The second toe may be included in the hallux sling 1 (FIG. 2) to increase the effect of the device as the windlass effect is mediated primarily by the first and second toes, but it is not required. Additionally, the hallux sling 1 (FIG. 2) remains articulated at the metatarsophalangeal joint 8 (FIG. 2), free from the remaining toes not incorporated into the hallux sling 1 (FIG. 2), to allow for independent dorsiflexion of the hallux 4 (FIG. 2), locking of the longitudinal arch, and tension to the plantar fascia. Dorsiflexion of the hallux 4 (FIG. 2) activates the Windlass effect by tensing the plantar fascia and locking the longitudinal arch of the foot.

The hallux sling 1 (FIG. 2) is secured to the ankle 5 (FIG. 2) via the ankle sling 2 (FIG. 2). The ankle sling 2 (FIG. 2) is another stiff elastic band, which is less stiff than the hallux sling 1 (FIG. 2), and it is wrapped around the ankle 5 (FIG. 2) to provide the force of dorsiflexion required to overcome some of the resting strength of the gastrocnemius-soleus complex and result in passive ankle dorsiflexion. It is this portion that will act like any traditional static ankle splint by maintaining the ankle 5 (FIG. 2) in a dorsiflexed position. The ankle sling 2 (FIG. 2) may be in continuity or adjustable to accommodate increased tension as well as large foot sizes. If adjustable, one or both sides of the sling can be pulled and wrapped behind the ankle 5 (FIG. 2) until appropriate fit and/or tension is achieved, and the sling can be fixed into position by securing the sides of the ankle sling 2 (FIG. 2) with an attachment device 6 (FIG. 4), including, but not limited to, tape, VELCRO® hoop and loop fastener, a zipper, or a snap. Because the hallux sling 1 (FIG. 2) is attached to the ankle sling 2 (FIG. 2) providing tension from the dorsal side of the hallux 4 (FIG. 2), dorsiflexion changes with tibiotalar motion. Hence, the more tibiotalar plantarflexion results in more hallux 4 (FIG. 2) dorsiflexion and vice versa. It is possible, but not required, that the hallux sling 1 (FIG. 2) and ankle sling 2 (FIG. 2) be made of the same material with a static elasticity or an elastic gradient as long as tension is applied in the dorsal direction at the hallux 4 (FIG. 2) and ankle 5 (FIG. 2). This allows the foot to come to a new equilibrium position at rest with the plantar fascia tensed and the longitudinal arch locked. The plantar fascia is tensed and longitudinal arch is locked independent of the position of the tibiotalar joint. However, the force applied to the plantar fascia can change with tibiotalar motion, alleviating the burning pain associated with a static stretch applied to the plantar fascia.

The remainder of the device can be filled in with a flexible material 3 (FIG. 2) to mimic a sock or left empty to mimic a splint depending on the desired design and function. The flexible material 3 or sock can be sewn into the hallux sling 1 and ankle sling 2, or a sock may fit, as shown in FIG. 6, underneath the hallux sling 1 and ankle sling 2. Being the most flexible and located on the plantar aspect of the hallux 1 (FIG. 2) proximal to the first metatarsophalangeal joint 8 (FIG. 2), this remaining material will not affect the function of the device as long as it remains more flexible than the hallux sling 1 (FIG. 2) or ankle sling 2 (FIG. 2). The device is designed to be simple and easily manufactured. The device retracts the big toe of the foot through use of a strap.

What is claimed is:

1. A foot splint for treating plantar fasciitis in a human foot, comprising:
  a band configured to be removably secured to a human foot, the band comprising
    a first portion configured to be wrapped around and secure a hallux but not the metatarsophalangeal joint in a human foot; and
    a second portion attached to the first portion and configured to be positioned over a dorsal side of the human foot, the second portion configured to wrap around an ankle of the human foot to secure the hallux in a dorsiflexed position and thereby tension a plantar fascia of the human foot by pulling on said first portion, the second portion extending from the first portion, configured to extend over a top of the human foot and around the ankle and to releasably fasten to itself, one or both of the first portion and second portion configured to define a helix when secured over the human foot,
  wherein the foot splint is configured for daily wear within a shoe during ambulation and allows a user to dynamically control an amount of tension applied to the plantar fascia by allowing the user to dorsiflex and plantarflex the ankle while wearing the splint.

2. The foot splint of claim 1, wherein the first portion is configured to fit over the hallux and the second toe of the human foot.

3. The foot splint of claim 1, wherein the band comprises an elastic material.

4. The foot splint of claim 1, wherein the second portion is releasably fastenable via a hoop and loop fastener.

5. The foot splint of claim 1, wherein the first and second portions, when fitted over the hallux and ankle of the natural human foot, do not secure the hallux in a fixed position or the ankle at a 90 degree angle, thereby allowing for dynamic splinting of the plantar fascia of the human foot.

6. The foot splint of claim 1, further comprising a garment attached to the first and second portions along a length of the first and second portions, the garment configured to fit over the human foot.

7. The foot splint of claim 6, wherein the first and second portions are disposed over the garment.

8. The foot splint of claim 6, wherein the garment is a sock.

9. A foot splint for treating plantar fasciitis, comprising:
  a first splint portion configured to fit over and support a hallux distal of the metatarsophalangeal joint in a human foot; and
  a second splint portion attached to the first splint portion, the second splint portion configured to releasably wrap around an ankle of the human foot to secure the hallux in a dorsiflexed position and thereby tension a plantar fascia of the human foot by pulling on a dorsal side of the first splint portion, one or both of the first and second splint portions defining a helix shape,
  wherein the foot splint allows a user to dorsiflex and plantarflex the ankle while wearing the splint, thereby allowing the user to dynamically control an amount of tension applied to the plantar fascia during use.

10. The foot splint of claim 9, wherein the first splint portion is configured to fit over the hallux and the second toe of the human foot.

11. The foot splint of claim 9, wherein one or both of the first and second splint portions comprises an elastic material.

12. The foot splint of claim 9, wherein the second splint portion is attached to the dorsal side of the first splint portion, and the second splint portion is configured to extend from said dorsal side of the first splint portion, over a top of the foot and around the ankle to fasten the splint to the ankle.

13. The foot splint of claim 9, wherein the second splint portion is configured to releasably fasten to itself via an attachment member.

14. The foot splint of claim 13, wherein the attachment member comprises a hoop and loop fastener.

15. The foot splint of claim 9, further comprising a cloth attached to the first and second splint portions along a length of the first and second splint portions, the cloth configured to fit over the human foot.

16. The foot splint of claim 15, wherein the first and second splint portions are disposed over the cloth.

17. The foot splint of claim 15, wherein the cloth is part of a sock.

* * * * *